United States Patent [19]

Schönafinger et al.

[11] Patent Number: 4,937,241

[45] Date of Patent: Jun. 26, 1990

[54] N-SUBSTITUTED N-NITROSOAMINOACETONITRILES, PROCESS FOR THEIR PREPARATION AND THEIR USE

[75] Inventors: Karl Schönafinger, Alzenau; Rudi Beyerle, Frankfurt; Helmut Bohn, Schöneck, all of Fed. Rep. of Germany

[73] Assignee: Cassella Aktiengesellschaft, Frankfurt, Fed. Rep. of Germany

[21] Appl. No.: 290,058

[22] Filed: Dec. 27, 1988

[30] Foreign Application Priority Data

Jan. 14, 1988 [DE] Fed. Rep. of Germany ....... 3800830

[51] Int. Cl.$^5$ ................ C07D 413/04; C07D 271/04; A61K 31/495; A61K 31/41

[52] U.S. Cl. ............................... 514/227.5; 544/58.1; 544/58.2

[58] Field of Search ...................... 544/58.1, 58.2, 163, 544/398; 546/312; 548/557; 514/227.5, 238.2, 255, 315, 329, 426

[56] References Cited

U.S. PATENT DOCUMENTS

| | | | |
|---|---|---|---|
| 3,312,690 | 4/1967 | Masuda et al. | 540/603 |
| 3,966,760 | 6/1976 | Schwan et al. | 548/371 |
| 4,002,652 | 1/1977 | Schwan et al. | 548/371 |
| 4,009,177 | 2/1977 | Schwan et al. | 548/371 |
| 4,014,878 | 3/1977 | Schwan et al. | 548/371 |
| 4,014,886 | 3/1977 | Schwan et al. | 548/371 |

FOREIGN PATENT DOCUMENTS

1795587  4/1972  Fed. Rep. of Germany .
2271818  12/1975  France .

*Primary Examiner*—Joseph Paul Brust
*Assistant Examiner*—MarySue Howard
*Attorney, Agent, or Firm*—Perman & Green

[57] ABSTRACT

Pharmacologically useful N-substituted-N-nitrosoaminoacetonitriles of the general formula I

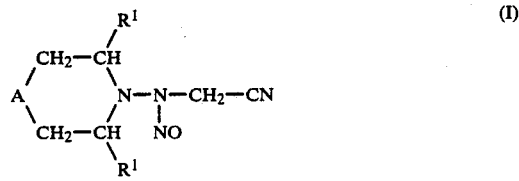

wherein A denotes the radical $-CH_2-$, $-O-$, $-S(O_n)-$, $-N(R^2)-$ or a direct bond, $R^1$ and $R^2$ denote alkyl having 1 to 4 c atoms or phenylalkyl having 1 to 4 C atoms in the alkyl radical, n denotes the number 0, 1 or 2, are prepared, for example, by nitrosylation of compounds of the general formula II

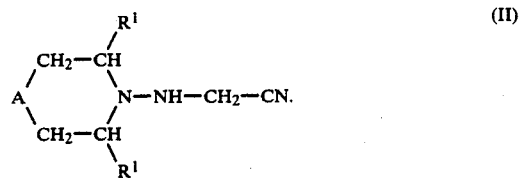

4 Claims, No Drawings

N-SUBSTITUTED N-NITROSOAMINOACETONITRILES, PROCESS FOR THEIR PREPARATION AND THEIR USE

The invention relates to pharmacologically active N-substituted N-nitrosoaminoacetonitriles of the general formula I

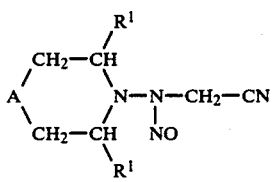

and their pharmacologically acceptable acid addition salts, wherein

A denotes the radical $-CH_2-$, $-O-$, $-S(O_n)-$, $-N(R^2)-$ or a direct bond, $R^1$ and $R^2$ denote alkyl having 1 to 4 C atoms or phenylalkyl having 1 to 4 C atoms in the alkyl radical, n denotes the number 0, 1 or 2.

The invention also relates to a process for the preparation of the compounds I according to the invention and their use.

Alkyl radicals can be straight-chain or branched. This also applies if they occur in connection with phenalkyl.

2 is preferred for n.

The direct bond and the divalent radicals: $-CH_2-$, $-O-$ and $-S(O_2)-$, of which the radical $-CH_2-$ is particularly preferred, are preferred for A.

The alkyl or phenalkyl radicals standing for $R^1$ and $R^2$ can be identical or different. Examples of suitable phenalkyl radicals standing for $R^1$ and/or $R^2$ are benzyl, 2-phenethyl, 3-phenylpropyl and 3-phenylbutyl. Examples of suitable alkyl radicals standing for $R^1$ and/or $R^2$ are methyl, ethyl, n-propyl, i-propyl, n-butyl, i-butyl and tert.-butyl. Methyl is preferred for $R^1$ and/or $R^2$.

Preferred compounds of the formula I are those in which A denotes a direct bond, $-O-$, $-CH_2-$ or $-S(O_2)-$ and $R^1$ denotes methyl.

A compound of the general formula I can be prepared by a process in which (a) a compound of the general formula II

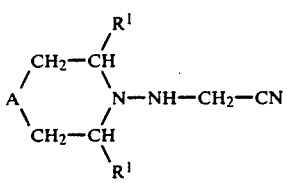

wherein A and $R^1$ have the meanings already mentioned, is nitrosylated, or in which (b) an acid addition salt of a substituted 3-aminosydnone imine of the formula III

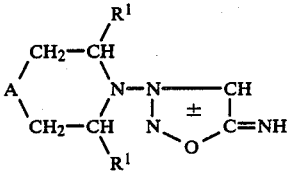

wherein A and $R^1$ have the meanings already mentioned, is reacted with a base and the compound obtained in the case in which A denotes $-N(R^2)-$ is converted, if appropriate, into a pharmacologically acceptable acid addition salt.

The nitrosylation of the compound of the formula II is carried out in a known manner, expediently in a suitable inert solvent or solvent mixture, preferably in water, normally at temperatures for 0° to 40° C. and preferably at temperatures from 0° to 10° C. The nitrosylation is carried out, for example, using nitrous acid, NO, NOCL or NO-containing gas mixtures. Expediently, the nitrosylation is carried out using nitrous acid which is advantageously produced from an alkali metal nitrite, for example sodium nitrite, and an acid, in particular hydrochloric acid. It is expedient to adjust the aqueous solution of the compound II to a pH of 1 to 3 using an acid, in particular hydrochloric acid, and to add the alkali metal nitrite dropwise in the form of an aqueous solution to the stirred and cooled solution of the compound.

Compounds of the formula I can also be prepared by a process in which an acid additon salt of a compound of the formula III, expediently in aqueous solution, is treated with a base, i.e. a compound which gives an alkaline reaction in water, such as, for example, an alkali metal hydroxide, such as, for example, lithium hydroxide, sodium hydroxide or potassium hydroxide, an alkali metal carbonate, such as, for example, lithium carbonate, potassium carbonate or sodium carbonate, or an alkali metal bicarbonate, such as, for example, sodium bicarbonate, or an amine, in particular a tertiary amine, such as, for example, triethylamine. The reaction is normally carried out at 10° to 40° C., preferably at room temperature. At least sufficient base is added to completely bind acid radical. As a rule, the acid addition salt is dissolved in water or a mixture of water and a solvent and sufficient base is added until the aqueous solution has an alkaline reaction. The binding of the acid radical can also be carried out using an ion-exchange resin.

The required starting compounds of the general formula II can be prepared by Strecker's aminonitrile synthesis in a manner known per se from compounds of the general formula IV

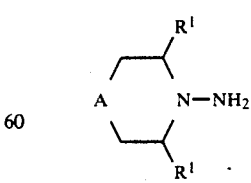

wherein A and $R^1$ have the meanings already mentioned, by reaction with formaldehyde and hydrocyanic acid or sodium cyanide in a suitable solvent, for example water, a compound of the general formula II resulting, which is converted into the compound I by nitrosylation. The compound I can be isolated from the solution of the compound I obtained in the course of this.

Starting compounds of the formula III can be prepared by a process in which a compound of the formula I or the solution produced in the nitrosylation of the compound II is cyclized. The cyclization of the compound I is carried out in a suitable organic or inorganic solvent, dispersant or diluent with the addition of a cyclizing agent, normally at temperatures from −10° to 40° C., in particular 0° to 40° C., preferably at 0° to 20° C.

Suitable cyclizing agents are those which give a pH of 3 or below in aqueous solution, i.e. for example strong acids, such as mineral acids, such as sulphuric, nitric or phosphoric acid, preferably hydrochloric acid, but also strong organic acids, such as sulphonic acids or trifluoroacetic acid. The cyclization is normally carried out with ice-cooling. 0.1 to 10 moles, preferably 1 to 5 moles, of the cyclizing agent are used, for example, relative to 1 mole of the compound of the formula I. The cyclizing agent is normally employed in excess. The use of hydrochloric acid as a cyclizing agent, which is normally introduced until the reaction batch saturated, is particularly convenient. An acid addition salt of the compound III is obtained directly in the cyclization.

Suitable solvents, dispersants or diluents are, for example: alcohols, for example those having 1 to 8 C atoms, in particular those having 1 to 6 C atoms, preferably those having 1 to 4 C atoms, such as, for example, methanol, ethanol, i- and n-propanol, i-, sec- and tert-butanol, n-, i-, sec-, tert-pentanol, n-hexanol, 2-ethylbutanol, 2-ethylhexanol, isooctyl alcohol, cyclopentanol, cyclohexanol, methylcyclohexanol (mixture), benzyl alcohol; ethers, in particular those having 2 to 8 C atoms in the molecule, such as, for example, diethyl ether, methyl ethyl ether, di-n-propyl ether, di-isopropyl ether, methyl n-butyl ether, methyl tert-butyl ether, ethyl propyl ether, di-butyl ether, tetrahydrofuran, 1,4-dioxane, 1,2-dimethoxyethane, bis-$\beta$-methoxyethyl ether; oligoethylene glycol dimethyl ethers, such as, for example, tetraglyme or pentaglyme; carboxylic acid alkyl esters, in particular those having 2 to 10 C atoms in the molducle, such as, for example, methyl, ethyl, butyl or isobutyl formate, methyl, ethyl, propyl, isopropyl, butyl, isobutyl or secbutyl, amyl, isoamyl, hexyl, cyclohexyl or benzyl acetate, methyl, ethyl or butyl propionate; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, methylcyclohexanone, dimethylcyclohexanone, benzophenone, acetophenone; aliphatic hydrocarbons, such as, for example, hexane, heptane, low- and high-boiling petroleum ethers, petroleum spirits and white spirit; cycloaliphatic hydrocarbons, such as, for example, cyclopentane, cyclohexane, methylcyclohexane, tetralin, decalin; aromatic hydrocarbons, such as, for example, benzene, toluene, o-, m- and p-xylene, ethyl benzene; halogenated aliphatic or aromatic hydrocarbons, such as, for example, methylene chloride, chloroform, carbon tetrachloride, 1,2-dichloroethane, chlorobenzene, dichlorobenzene; hexamethylphosphoric triamide; sulphoxides, such as, for example, dimethyl sulphoxide; tetramethylene sulphone; water. Mixtures of various solvents or dispersants can also be used, for example water-methanol or, preferably, ethyl acetate-methanol.

The solution of the compound I produced in the nitrosylation of the compound II can be subjected directly to the cyclization reaction. However, it is normally appropriate, for the subsequent cyclization, to take up the nitroso compound I first in a suitable organic solvent and to carry out, if appropriate after addition of a further solvent, the cyclization to the compound of the formula III in it. It may be expedient for, the preparation of a compound of the formula I, not to isolate the compound I directly from the solution of the compound I produced in the nitrosylation of the compound II, but to cyclize to give a compound of the formula III and to obtain the compound of the formula I from this.

The compounds of the formula I according to the invention can exist in various configurations in the cisor trans-form, it being possible for the trans-forms to exist as racemic mixtures or in optically active form. For the preparation of these various isomers, processes known per se, such as selective synthesis, chiral synthesis or resolution of racemic mixtures according to known methods can be used.

The compounds of the general formula I can form acid addition salts with inorganic or organic acids, in the case in which A denotes $-N(R^2)-$. Inorganic or organic acids are suitable for the formation of acid addition salts of this type. Suitable acids are, for exmaple, hydrochloric acid, hydrobromic acid, phosphoric acid, nitric acid, sulphuric acid, oxalic acid, lactic acid, tartaric acid, acetic acid, salicylic acid, benzoic acid, formaic acid, propionic acid, pivalic acid, diethylacetic acid, malonic acid, succinic acid, pipelic acid, fumaric acid, maleic acid, malic acid, sulphamic acid, phenylpropionic acid, gluconic acid, ascorbic acid, isonicotinic acid, methanesulphonic acid, p-toluenesulphonic acid, citric acid, adipic acid or naphthalenedisulphonic acis, in particular naphthalene-1,5-disulphonic acid. Pharmacologically acceptable acid addition salts are preferred. The acid addition salts can be prepared as customary by combining the components, expediently in a suitable solvent or diluent.

The compounds of the general formula IV are known in some cases (compare, for example, C. G. Overberger et al, J. Ameri. Chem. Soc. 77, (1955) 4100) or can be prepared, starting from compounds of the general formula V

(V)

by a process in which either (a) a compound of the formula V is nitrosylated to the N-nitroso compound VI and is subsequently reduced, expediently using lithium aluminium hydride:

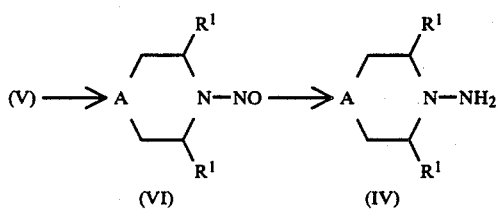

or in which in a manner known per se (b) a compound of the formula V is converted, using potassium cyanate in acidic medium, into the urea derivative VII, which is then converted into the compound IV by oxidation with sodium hydrochlorite by the Hoffmann degradation:

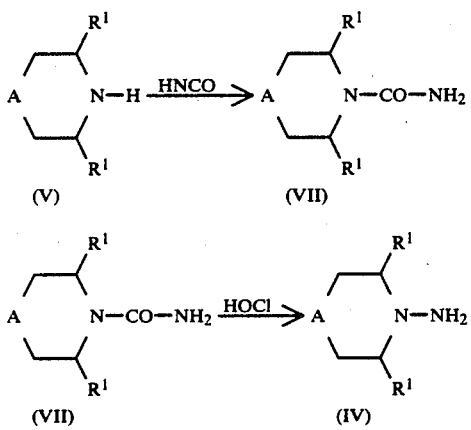

Starting compounds of the formula V are known (compare, for example, Backer, vn der Ley, Rec. Trav. Chim. Pays-Bas 70, (1951) 564; Berlin, Sytschewa, Z. obsc. Chim. 20, (1950) 640; Idson, Spoerri, J. Amer. Chem. Soc. 76, (1954) 2902) or can be prepared by the processes known for these classes of compound. Thus, compounds of the formula V can be prepared, for example, by ring closure with ammonia from compounds of the general formula VIII

wherein A denotes —SO— or —S($O_2$)— and $R^{1*}$ denotes a radical which is transormed into the radical $R^1$ already mentioned by addition of hydrogen in the reaction with ammonia, and which can be prepared by methods known per se. The reaction with ammonia can be carried out at temperatures of 20° to 150° C., preferably at 60° to 100° C., with or without solvent.

If the reaction of the compounds of the formula VIII is carried out not with ammonia but with hydrazine under the conditions previously mentioned, the compounds of the formula IV can be obtained directly in the ring closure.

The compound of the general formula I and its possible pharmacologically acceptable acid addition salts have useful pharmacological properties. Their action on the cardiovascular system is particularly pronounced. Compared with known sydnone imine compounds substituted in the 3-position, for example those of EP-B-59,356, and the commercially available compound molsidomine, they surprisingly possess, for example, a substantially longer duration of action. They lower, for example, the blood pressure as well as the pulmonary arterial pressure and the left ventricular end-diastolic pressure and thus contribute to a relief in the strain on cardiac activity within the meaning of an antianginal action, without provoking a reflex tachycardia during the course of this.

The compounds of the formula I and their possible pharmacologically acceptable acid addition salts can therefore be administered to humans as medicaments alone, in mixtures with one another or in the form of pharmaceutical preparations which permit enteral or parenteral use and which contain as active constituent an effective dose of at least one compound of the formula I or an acid addition salt thereof in addition to customary pharmaceutically acceptable excipients and additives.

The medicaments can be administered orally, for example in the form of pills, tablets, coated tablets, dragees, hard and soft gelatin capsules, solutions, syrups, emulsions or suspensions or aerosol mixtures. However, administration can also be carried out rectally, for example in the form of suppositories, or parenterally, for example in the form of injection solutions, or percutaneously, for example in the form of ointments or tictures. The pharmaceutical products contain the active compound of formula I or pharmaceutically-acceptable acid-addition salts thereof from about 0.5 to 90 percent by weight.

For the preparation of the pharmaceutical preparations, pharmaceutically inert inorganic or organic excipients can be used. For the preparation of pills, tablets, dragees and hard gelatin capsules, for example, lactose, maize starch or derivatives thereof, talc, stearic acid or its salts etc. can be used. Excipients for soft gelatin capsules and suppositories are, for example, fats, waxes, semisolid and liquid polyols, native or solidified oils etc. Suitable excipitents for the preparation of solutions and syrups are, for example, water, saccharose, invert sugar, glucose, polyols etc. Suitable excipients for the preparation of injection solutions are, for example, water alcohols, glycerol, polyols or vegetable oils.

The pharmaceutical preparations may contain additives, such as, for example, fillers, extendes, disintegrants, binders, lubricants, wetting agents, stabilizers, emulsifiers, preservatives, sweeteners, colourants, flavourings or aromatizers, buffer substances, further solvents or solubilizers or agents to achieve a depot effect, and also salts for alteration of the osmotic pressure, coating agents or antioxidants, in addition to the active compounds and excipients. They can also contain two or more compounds of the formula I or their pharmacologically acceptable acid addition salts and yet other therapeutically active substances.

Other therapeutically active substances of this type are, for example: β-receptor blockers, such as, for example, propranolol, pindolol, methoprolol; vasodilators, such as, for example, carbocaromene; sedatives, such as, for example, barbituric acid derivatives, 1,4-benzodiazepines and meprobamate; diuretics, such as, for example, chlorothiazide; agents affecting cardiac tone, such as, for example, digitalis preparations; hyprotensives, such as, for example, hydralazine, dihydralazine, prazosine, clonidine, Rauwolfia alkaloids; agents which lower the fatty acid level in the blood, such as, for example, bezafibrate, fenofibrate; agents for the propylaxis of thromboses, such as, for example, phenprocoumon.

The compounds of the formula I, their pharmacologically acceptable acid addition salts and pharmaceutical preparations, which contain the compounds of the formula I or their pharmacologically acceptable acid addition salts as active compounds, can be used in humans for the control or prophylaxis of disorders of the cardiovascular system, for example as antihydpertensive medicaments in the various forms of high blood pressure, and in the control or propylxis of angina pectoris etc. The dosage may vary within wide limits and is adjusted to the individual conditions in each separate case. In general, a daily dose of about 0.5 to 100 mg, preferably 1 to 20 mg, per human individual is adequate on oral administration. The daily dose with other forms of adminstration, on account of the good absorption of the active compounds, is also in a similar range, i.e. in general likewise at 0.5 to 100 mg/human. The daily dose is normally divided up into a number, for example 2 to 4, of part adminsitrations.

For the detection of the antianginal action of the compounds according to the invention, investigations were carried out on mongrel dogs of both sexes under pentobarbital anaesthesia (30 to 40 mg/kg i.v.) or under urethane-chloralose anaesthesia (3 ml/kg of urethane-chloralose mixture i.v.=20 mg/kg of chloralose and 250 mg/kg of urethane). The ventilation of the animals was carried out using a Bird Mark 7 respirator. The end-expiratory carbonic acid content (measured with an infrared absorption recorder) was between 4.5 and 5% by volume. During the entire experiment the animals under pentobarbital anaesthesia received a continuous infusion of pentobarbital i.v.=4 mg (in 6 ml)/kg/h, in order to ensure a constant depth of anaesthesia. The animals under urethane-chloralose anaesthesia received no continuous infusion. The infusion was given through the cephalic vein. After the preparation of the experimental animals there was a wait for about 1 hour until all haemodynamic parameters had settled (steady state). The actual experiment was then begun.

For the determination of the mean peripheral blood pressure (=BP), the systolic and diasolic blood pressure were measured peripherally in the femoral artery via a Statham pressure transducer. A Millar tip catheter pushed into the left ventricle via the carotid artery gave the signal for the left ventricular end-diastolic pressure (=LVEDP) and the heart rate (=HR).

the results obtained are indicated in the table below.

| Substance | Dose mg/kg | BP Δmm Hg | LVEDP Δmm Hg | HR Δb/min | DA min |
|---|---|---|---|---|---|
| A | 0.3 | −35 | −3 | +6 | 150 |
| Mol | 0.1 | −18 | −2.3 | +3 | 90 |

In the preceding table:
A=N-(2,6-dimethylpiperidine-1-yl)-N-nitrosoaminoacetonitrile
Mol=Comparison substnace molsidomine (3-(morpholin-1-yl)-N-ethoxycarbonyl-sydnoneimine)
BP=Mean peripheral blood pressure
LVEDP=Left ventricular end-diastolic pressure
HR=Heart rate (b/min=beats per minute)
DA=Duration of action In the examples below, unless stated otherwise, percentages are indicated in percentages by weight. Ratios indicated between components of solvents or eluents are ratios by volume. The statement "dec." denotes decomposition.

EXAMPLE 1

3-(3,5-Dimethylthiomorpholine 1,1-dioxid-4-yl)-N-nitrosoaminoacetonitrile (a) A mixture of 32.2 g of diallyl sulphone, 55 g of hydrazine hydrate and 54 ml of water is heated to boiling for 30 minutes. The batch is stirred in an ice bath, and the precipitate is filtered off with suction and recrystallized from ethanol.

Yield: 16.2 g of 4-amino-3,5-dimethylthiomopholine dioxide

Melting point: 181° to 183° C.

(b) A mixture of 16.2 g of 4-amino-3,5-dimethylthiomorpholine dioxide, 9.1 g of conc. hydrochloric acid, 80 ml of water and 5.6 g of sodium cyanide is cooled to 5° C. and 9.1 g of a 39% strength foraldehyde solution are added (pH=7 to 7.5). The reaction mixture is then stirred at room temperature for 4 hours. The mixture is rendered acidic (pH=1) with ice cooling and a solution of 6.3 g of sodium nitrite in 25 ml of water is added dropwise. The mixture is subsequently stirred at room temperature for 3 more hours and the solid is filtered off with suction.

Yield: 16.0 g of N-(3,5-dimethylthiomorpholine 1,1-dioxid-4-yl)-N-nitrosoaminoacetonitrile Melting point: 163° to 165° C.

EXAMPLE 2

N-(2,6-Dimethylpiperidin-1-yl)-N-nitrosoaminoacetonitrile 6 g of $NaHCO_3$ are added to an aqueous solution of 11.5 g of 3-(2,6-dimethylpiperidin-1-yl)-sydnone imine hydrochloride and the mixture is stirred for 2 hours. The product is extracted by shaking with ethyl acetate, and the organic phase is separated off, dried and concentrated. The residue is stirred with petroleum ether and filtered off with suction.

Yield: 6.5 g Melting point: 90°–91° C.

The required starting product 3-(2,6-dimethylpiperidin-1-yl)-sydnone imine hydrochloride is prepared as follows:

(a) A solution of 11.5 g of sodium cyanide in 20 ml of water is added to an ice-cooled mixture of 30.0 g of 1-amino-2,6-dimethylpiperidine, 20 g of conc. hydrochloric acid and 100 ml of water and the pH is adjusted to 6.5 using hydrochloric acid. 19.3 g of a 39% strength aqueous formaldehyde solution are then added and the reaction mixture is stirred at 0° C. for 3 hours and at room temperature for a further 3 hours. The product is extracted using ethyl acetate, and the ethyl acetate phase is washed with diluted glacial acetic acid and dried over sodium sulphate. After concentration an oily residue of 29.1 g of 3-(2,6-dimethylpiperidin-1-yl)-aminoacetonitrile remains, which is further processed as follows without further purification:

(b) A solution of 13.4 g of sodium nitrite in 10 ml of water is added dropwise to a mixture of 29.1 g of N-(2,6-dimethylpiperidin-1-yl)-aminoacetonitrile, 100 ml of water, 100 ml of ethyl acetate and 12 g of conc. hydrochloric acid and after stirring for 5 hours at room temperature the organic phase is separated off, diluted with 20 ml of methanol and stirred in an ice bath. After introducing hydrochloric acid until saturation, the mixture is subsequently stirred at room temperature for 15 hours and concentrated in a water-jet vacuum. The residue crystallizes on stirring with diethyl ether. It is filtered off with suction and recrystallized from acetonitrile.

Yield: 18.2 g of 3-(2,6-dimethylpiperidin-1-yl)sydnone imine hydrochloride

Melting point: 136°–137° C. (dec.)

Pharmaceutical preparations are described in Examples A to F below.

EXAMPLE A

Soft gelatin capsules, containing 5 mg of active compound per capsule:

|  | per Capsule |
|---|---|
| Active compound | 5 mg |
| Triglyceride mixture fractionated from coconut fat | 150 mg |
| Capsule content | 155 mg |

EXAMPLE B

Injection solution, containing 1 mg of active compound per ml:

|  | per ml |
|---|---|
| Active compound | 1.0 mg |
| Polyethylene glycol 400 | 0.3 ml |
| Sodium chloride | 2.7 mg |
| Water for injection | ad 1 ml |

EXAMPLE C

Emulsion, containing 3 mg of active compound per 5 ml

|  | per 100 ml of Emulsion |
|---|---|
| Active compound | 0.06 g |
| Neutral oil | q.s. |
| Sodium carboxymethylcellulose | 0.6 g |
| Polyoxyethylene stearate | q.s. |
| Glycerol, pure | 0.2 to 2.0 g |
| Flavouring | q.s. |
| Water (deionized or distilled) | ad 100 ml |

EXAMPLE D

Rectal medicament, containing 4 mg of active compound per suppository

|  | per Suppository |
|---|---|
| Active compound | 4 mg |
| Suppository base | ad 2 g |

EXAMPLE E

Tablets, containing 2 mg of active compound per tablet

|  | per Tablet |
|---|---|
| Active compound | 2 mg |
| Maize starch | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl starch | 25 mg |
|  | 309 mg |

EXAMPLE F

Dragees, containing 1 mg of active compound per dragee

|  | per Dragee |
|---|---|
| Active compound | 1 mg |
| Maize starch | 100 mg |
| Lactose | 60 mg |
| Calcium hydrogen phosphate | 30 mg |
| Soluble starch | 3 mg |
| Magnesium stearate | 2 mg |
| Colloidal silica | 4 mg |
|  | 200 mg |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We calim:

1. N-Substituted-N-nitrosoaminoacetronitriles of the general formula I

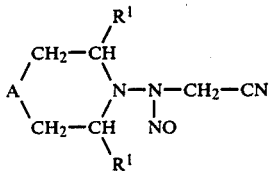

and their pharmacologically acceptable acid addition salts, wherein A is $-S(O_2)-$, and $R^1$ is selected from the group consisting of alkyl having 1 to 4 C atoms and phenylalkyl having 1 to 4 C atoms in the alkyl radical.

2. N-(2,6-Dimethylthiomorpholine 1,1-dioxid-4-yl)-N-nitrosoaminoacetonitrile.

3. A pharmaceutical product useful for controlling and/or preventing cardiovascular diseases and having, as active component, from about 0.5 to 90 percent by weight of a compound of claim 1 or of a pharmaceutically-acceptable acid-addition salt thereof together with a pharmaceutically-acceptable vehicle and, optionally, a pharmaceutically-acceptable inert additive.

4. A process for controlling or preventing cardiovascular diseases which comprises administering an effective amount of a pharmaceutically-acitve N-substituted-N-nitrosoaminoacetonitrile of claim 1, or of a pharmaceutically-acceptable acid-addition salt thereof, to a host which is afflicted with one or more of these conditions.

* * * * *